United States Patent
Jain et al.

(10) Patent No.: US 9,235,908 B2
(45) Date of Patent: Jan. 12, 2016

(54) REMOVAL OF ARTIFACTS FROM AN EM FIELD GENERATOR FROM A 3D SCAN

(71) Applicant: KONINKLIJKE PHILIPS N.V., Eindhoven (NL)

(72) Inventors: Ameet Kumar Jain, New York, NY (US); Raymond Chan, San Diego, CA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/364,431

(22) PCT Filed: Dec. 27, 2012

(86) PCT No.: PCT/IB2012/057741
§ 371 (c)(1),
(2) Date: Jun. 11, 2014

(87) PCT Pub. No.: WO2013/098767
PCT Pub. Date: Jul. 4, 2013

(65) Prior Publication Data
US 2014/0334744 A1    Nov. 13, 2014

Related U.S. Application Data

(60) Provisional application No. 61/580,509, filed on Dec. 27, 2011.

(51) Int. Cl.
*G06T 11/00* (2006.01)
*G06T 5/00* (2006.01)
*G06T 5/50* (2006.01)
(Continued)

(52) U.S. Cl.
CPC ............... *G06T 11/008* (2013.01); *A61B 6/488* (2013.01); *A61B 6/5252* (2013.01); *A61B 6/5258* (2013.01); *G06T 5/005* (2013.01); *G06T 5/50* (2013.01); *G06T 11/005* (2013.01); *A61B 6/12* (2013.01); *A61B 6/4085* (2013.01); *A61B 6/4441* (2013.01); *A61B 2019/5251* (2013.01);
(Continued)

(58) Field of Classification Search
CPC ................... A61B 19/5244; A61B 2019/5251; A61B 6/037; A61B 6/5258; A61B 6/547; A61B 6/582; A61B 6/12; A61B 6/4085; A61B 6/488; G06T 2211/424; G06T 11/005; G06T 11/008; G06T 2207/10081; G06T 2207/10116
See application file for complete search history.

(56) References Cited

U.S. PATENT DOCUMENTS 6,064,073 A * 5/2000 Hoogenraad ................. 250/573
8,023,767 B1   9/2011 Ning et al.
(Continued)

FOREIGN PATENT DOCUMENTS

EP   1302874   4/2003
EP   1627601   6/2008
(Continued)

*Primary Examiner* — Jingge Wu

(57) ABSTRACT

A method, system, and program product are provided for removing artifacts from an EM field generator from a rotational 3D scan. The method comprises: preoperatively, characterizing the artifacts from the EM field generator over a range of rotational positions of an x-ray source and detector; intraoperatively, determining the position of the EM field generator relative to the x-ray source and detector; and removing the preoperatively characterized artifacts for the determined relative position of the EM field generator from current x-ray image.

15 Claims, 3 Drawing Sheets

(51) Int. Cl.
*A61B 6/12* (2006.01)
*A61B 6/00* (2006.01)
*A61B 19/00* (2006.01)

(52) U.S. Cl.
CPC ............. *G06T2207/10081* (2013.01); *G06T 2207/10116* (2013.01); *G06T 2207/20224* (2013.01)

(56) References Cited

U.S. PATENT DOCUMENTS

| | | | |
|---|---|---|---|
| 8,588,497 B2 * | 11/2013 | Dennerlein et al. | 382/131 |
| 2002/0191734 A1 * | 12/2002 | Kojima et al. | 378/4 |
| 2004/0054248 A1 * | 3/2004 | Kimchy et al. | 600/3 |
| 2006/0008051 A1 * | 1/2006 | Heaton et al. | 378/57 |
| 2006/0020200 A1 * | 1/2006 | Medow et al. | 600/425 |
| 2006/0227928 A1 * | 10/2006 | Timmer | 378/4 |
| 2006/0237652 A1 * | 10/2006 | Kimchy et al. | 250/363.02 |
| 2008/0082363 A1 | 4/2008 | Habashi | |
| 2008/0162393 A1 | 7/2008 | Iliff | |
| 2009/0012373 A1 | 1/2009 | Raij et al. | |
| 2010/0183214 A1 | 7/2010 | McCollough et al. | |
| 2011/0075899 A1 * | 3/2011 | Kunze et al. | 382/128 |
| 2011/0109311 A1 * | 5/2011 | Walsh | 324/309 |
| 2011/0229007 A1 * | 9/2011 | Jerebko | 382/132 |
| 2012/0172709 A1 * | 7/2012 | Nalcioglu et al. | 600/411 |
| 2014/0350387 A1 * | 11/2014 | Siewerdsen et al. | 600/424 |

FOREIGN PATENT DOCUMENTS

| | | |
|---|---|---|
| WO | WO2009097580 | 8/2009 |
| WO | WO2012155050 | 11/2012 |

* cited by examiner

REMOVAL OF ARTIFACTS FROM AN EM FIELD GENERATOR FROM A 3D SCAN

CROSS-REFERENCE TO PRIOR APPLICATIONS

This application is the U.S. National Phase application under 35 U.S.C. §371 of International Application Serial No. PCT/IB2012/057741, filed on Dec. 27, 2012, which claims the benefit of U.S. application Ser. No. 61/580,509, filed on Dec. 27, 2011. These applications are hereby incorporated by reference herein.

FIELD OF THE INVENTION

The invention relates to the field of medical imaging and more particularly to a method, system and computer program product for removing artifacts from an EM field generator from a 3D scan.

BACKGROUND

The principle behind electro-magnetic (EM) tracking is that a field generator produces spatially varying magnetic fields which induce currents in sensor coils. A measurement system is then used to calculate the position and orientation of the sensors, based on measured voltages in the sensors. EM tracking techniques provide real-time position and orientation information in 3D space, which may be used to aid interventional procedures. Since the size of these sensor coils is very small, they can be embedded into a catheter or other surgical tool and be used for guided navigation. As a result, EM tracking systems are very well suited to in-body interventions.

When electromagnetic tracking is used in conjunction with x-ray imaging, such as in a cathlab, the electromagnetic (EM) tracking field generators can corrupt the x-ray images, particularly rotational images from a cone beam CT scan. Even though efforts have been made to design x-ray compatible field generators that do not show any large electronic components in the x-ray image, there are still features that can produce artifacts that are visible on the x-ray image. These features include wires that run from the top to the bottom of the field generator and sharp edges of the outer and inner casings of the field generator. These features typically cause artifacts in the shape of lines on the x-ray image.

SUMMARY

A method, system and program product are provided for removing artifacts from an EM field generator from a rotational 3D scan.

According to one aspect of the present invention, a method is provided for removing artifacts from an EM field generator from a rotational 3D scan. The method comprises the steps of: preoperatively, characterizing the artifacts from the EM field generator over a range of rotational positions of an x-ray source and detector; intraoperatively, determining the position of the EM field generator relative to the x-ray source and detector; and removing the preoperatively characterized artifacts for the determined relative position of the EM field generator from a current x-ray image.

According to one embodiment, characterizing the artifacts comprises determining the attenuation coefficients for each voxel of each artifact at each rotational position and wherein removing the preoperatively characterized artifacts comprises subtracting the attenuation coefficients from a current x-ray image.

According to one embodiment, the method for removing artifacts from an EM field generator from a rotational 3D scan further comprises the step of presenting the current x-ray image on a display with the artifacts removed.

According to one embodiment, characterizing the artifacts further comprises determining the shape of each artifact.

According to one embodiment, the shape of each artifact is determined by defining the artifacts using an edge detection process.

According to another aspect of the present invention, a system is provided for removing artifacts from an EM field generator from a rotational 3D scan. The system comprises: a processor; a memory operably connected to the processor; and a program of instruction encoded on the memory and executed by the processor. When executed, the program of instruction preoperatively characterizes the artifacts from the EM field generator over a range of rotational positions of an x-ray source and detector, intraoperatively determines the position of the EM field generator relative to the x-ray source and detector, and removes the preoperatively characterized artifacts for the determined relative position of the EM field generator from a current x-ray image.

According to one embodiment, the system further comprises a display operably connected to the processor, wherein the program of instruction when executed by the processor presents the current x-ray image on a display with the artifacts removed.

According to another aspect of the present invention, a computer program product is provided comprising a computer readable storage device having encoded thereon a computer executable program of instruction for removing artifacts from an EM field generator from a rotational 3D scan. The program of instruction comprises: program instructions for preoperatively, characterizing the artifacts from the EM field generator over a range of rotational positions of an x-ray source and detector; program instructions for intraoperatively, determining the position of the EM field generator relative to the x-ray source and detector; and program instructions for removing the preoperatively characterized artifacts for the determined relative position of the EM field generator from a current x-ray image.

BRIEF DESCRIPTION OF THE DRAWINGS

The features and advantages of the invention will be more clearly understood from the following detailed description of the preferred embodiments when read in connection with the accompanying drawing. Included in the drawing are the following figures.

DETAILED DESCRIPTION

The present invention provides a method, system, and computer program product for removing artifacts from an EM field generator from a 3D scan. According to one embodiment of the present invention, artifacts from the EM field generator are preoperatively characterized over a range of rotational positions of an x-ray source and detector. Then, the position of the EM field generator relative to the x-ray source and detector is determined intraoperatively, and the preoperatively characterized artifacts for the determined relative position of the EM field generator are removed from the current image.

Figure 1:
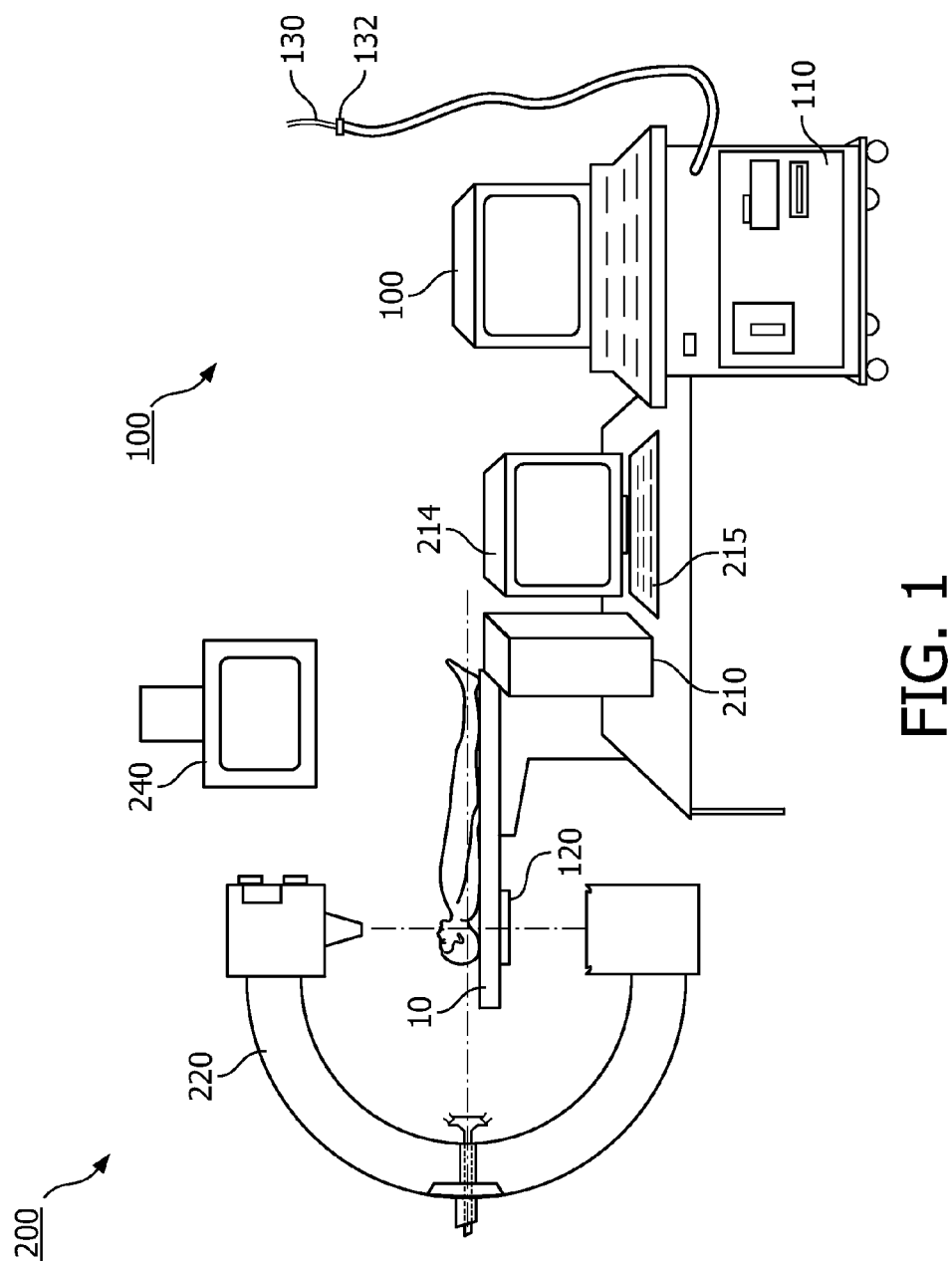
FIG. 1 is an isometric view of a system for removing artifacts from an EM field generator from a 3D scan according to an embodiment of the present invention.

FIG. 1 shows a system for removing artifacts from an EM field generator from a 3D scan according to an embodiment of the present invention. The system comprises: an EM tracking system 100, and an x-ray system 200, which may be operated concurrently. The EM tracking system 100 is used for tracking the location of a tool during a surgical procedure, typically a catheter, during a catheter intervention. The x-ray system 200 is used for visualizing internal structures, fluid movement, tissue movement, and the like during the surgical intervention. The EM tracking system 100 includes a field generator 120 which can cause artifacts in the x-ray images, particularly if the x-ray images are rotational scans such as a cone beam CT.

The x-ray system 200 comprises an x-ray machine 220 disposed for taking x-ray images of a patient on a table 10. According to one embodiment, the x-ray machine is a C-arm scanner.

A processing unit 210, such as a general purpose computer is operably connected to the x-ray machine and processes x-ray images from the x-ray machine 220. The processed image may be presented on a display 214.

The system also comprises an electromagnetic (EM) tracking system 100 for tracking a surgical tool in real time during a surgical procedure. The EM tracking system 100 comprises a processing unit 110 for processing electromagnetic tracking data, a sensor 132 comprising a conductive coil for sensing electromagnetic fields, and a field generator 120 that generates electromagnetic fields. The sensor 132 is connected to a surgical tool 130, such as a catheter.

The processing unit 110 of the EM tracking system calculates the position of the tool 130 in 3D space using the voltages generated in the sensor 132 due to the magnetic field generated by the field generator 120. The EM tracking system 100 is registered to the x-ray system 200, by a calibration procedure, for example. A representation of the tool 130 can be overlaid onto the x-ray image or a model generated from the x-ray system by the processing unit 210 of the x-ray system using the tracked location. The x-ray image with overlaid tool may be presented on a display 240.

Figure 2:
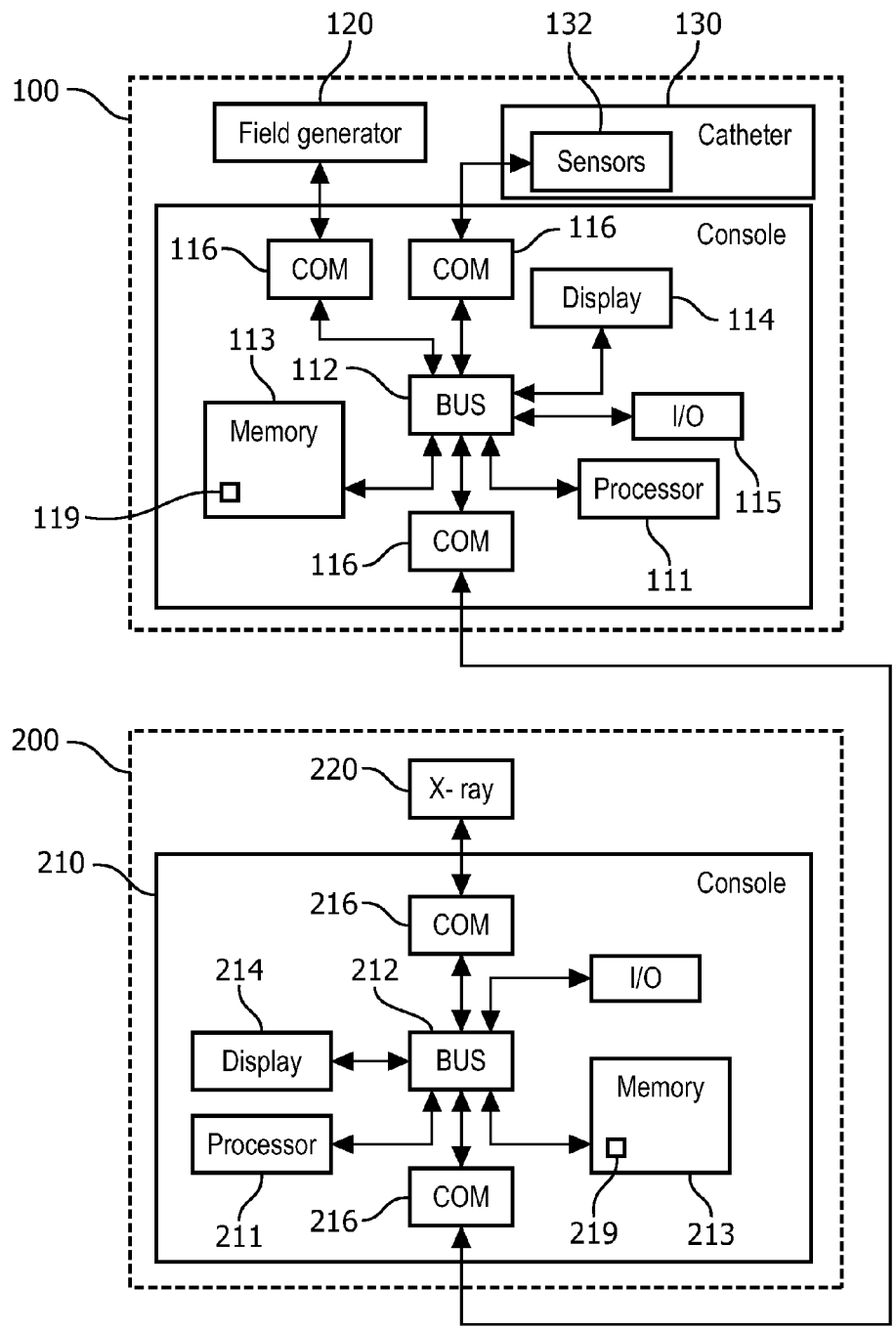
FIG. 2 is a block diagram of a system for removing artifacts from an EM field generator from a 3D scan according to an embodiment of the present invention.

FIG. 2 is a block diagram of the system for removing artifacts from an EM field generator from a 3D scan according to an embodiment of the present invention. The EM tracking system 100 comprises a processing unit 110 (FIG. 1), a field generator 120 and a sensor 132. The processing unit 110 comprises a processor 111 and a memory 113. The processor 111 is operably connected to the memory 113. According to one embodiment, they are connected through a bus 112. The processor 111 may be may be any device capable of executing program instructions, such as one or more microprocessors. Moreover, the processor 111 may be embodied in a general purpose computer.

The memory 113 may be any volatile or non-volatile memory device suitable for storing data and program instructions, such as a removable disc, a hard drive, a CD, a Random Access Memory (RAM), a Read Only Memory (ROM), or the like. Moreover, the memory 113 may comprise one or more memory devices.

The processing unit 110 may further comprise one or more network connectors 116 for sending or receiving x-ray and other data. The network connectors 116 may be Uniform Serial Bus (USB) connectors, internet adapters, or any other connector suitable for receiving data from another device, either directly or through a network, such as an intranet or the Internet.

The processing unit 110 may also comprise a display 114, such as a monitor for displaying tracking images, anatomic models, and the like. One or more monitors may be provided, either in addition to or in place of dedicated monitors for the EM tracking system 100 and for the x-ray system 200.

Additional input and/or output devices (I/O) 115, such as a keyboard, a mouse, or the like may be provided as part of a user interface to receive indications from a user, such as selection of a point and navigation within an image on the display 114.

The memory 113 has encoded thereon, a program of instruction 119 executable by the processor 111 to process and display EM tracking data, such as the location of the sensor 132 on a surgical tool 130 overlaid on an image or model from x-ray imaging.

The x-ray system 200 also comprises a processing unit 210. Processing unit 210 is operably connected to an x-ray machine 220, such as through network connectors 216.

The processing unit 210 of the x-ray system 200 comprises a processor 211 and a memory 213. The processor 211 is operably connected to the memory 213. According to one embodiment, they are connected through a bus 212. The processor 211 may be any device capable of executing program instructions, such as one or more microprocessors. Moreover, the processor 211 may be embodied in a general purpose computer.

The memory 213 may be any volatile or non-volatile memory device suitable for storing data and program instructions, such as a removable disc, a hard drive, a CD, a Random Access Memory (RAM), a Read Only Memory (ROM), or the like. Moreover, the memory 213 may comprise one or more memory devices.

The processing unit 210 may further comprise one or more network connectors 216 for sending or receiving x-ray and other data. The network connectors 216 may be Uniform Serial Bus (USB) connectors, internet adapters, or any other connector suitable for receiving data from another device, either directly or through a network, such as an intranet or the Internet.

The processing unit 210 may also comprise a display 214, such as a monitor for displaying x-ray images, anatomic models, and the like. One or more monitors may be provided, either in addition to or in place of dedicated monitors for the EM tracking system 100 and for the x-ray system 200.

Additional input and/or output devices (I/O), such as a keyboard, a mouse, or the like may be provided as part of a user interface to receive indications from a user, such as selection of a point and navigation within an image on the display 214.

The memory 213 has encoded thereon, an x-ray program of instruction 219 executable by the processor 211 to remove artifacts from an EM field generator from a 3D x-ray scan. According to one embodiment the x-ray images are rotational scan images such as from a cone beam CT scan.

Figure 3:
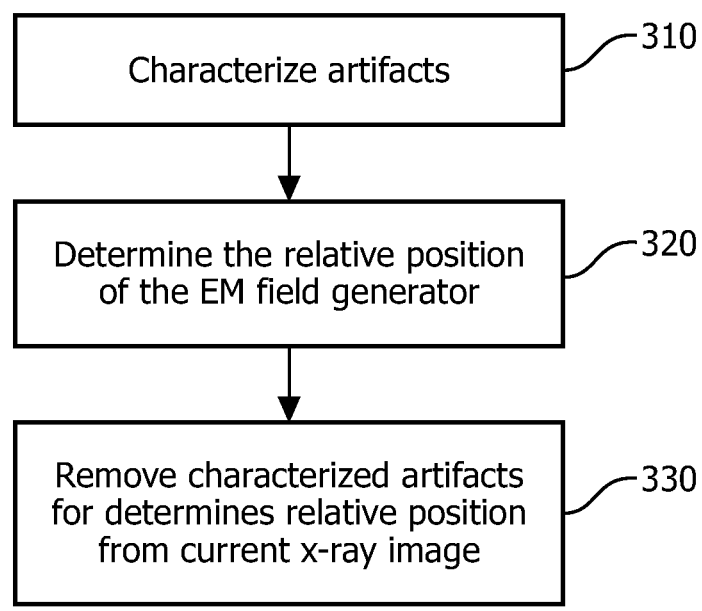
FIG. 3 is a flow diagram of a method for removing artifacts from an EM field generator from a 3D scan according to an embodiment of the present invention.

FIG. 3 is a flow diagram of a method for removing artifacts from an EM field generator from a 3D scan according to an embodiment of the present invention. Preoperatively, the x-ray program of instruction 219 executed by the x-ray processor 211 characterizes the artifacts from the EM field generator over a range of rotational positions of the x-ray source and detector (Step 310). The characterization may comprise recording intensity values or attenuation coefficients for each voxel of an x-ray image at each rotational position of the x-ray machine 220. The attenuation coefficients are stored with their respective locations for each rotational position of the x-ray machine 220 relative to the field generator 120.

The x-ray machine is set at a known rotational position without a patient on the table 10. Then, an x-ray image is generated, and the attenuation coefficients or intensity values are determined for each voxel and stored in memory 213 or another memory.

Intraoperatively, the x-ray program of instruction 219 executed by the x-ray processor 211 determines the position of the EM field generator 120 relative to the x-ray machine 220 source and detector (Step 320). Since the location of the source and detector are typically known relative to the table 10, and the field generator 120 is at known position relative to the table 10, this requires a simple translation, as is known in the art.

Then, the x-ray program of instruction 219 executed by the x-ray processor 211 removes the preoperatively characterized artifacts for the determined relative position of the EM field generator 120 from the current x-ray image (Step 330). To remove the artifacts, the stored intensity values for each voxel are subtracted from the corresponding voxel in the current x-ray image.

The x-ray program of instruction 219 executed by the x-ray processor 211 presents the resulting current x-ray image on a display with the artifacts removed. According to one embodiment, the x-ray program of instruction 219 executed by the x-ray processor 211 uses an edge detection process to locate artifacts and determine their shape. Then, attenuation coefficients are only determined and stored for the voxels of the artifacts.

The invention can take the form of an entirely hardware embodiment or an embodiment containing both hardware and software elements. In an exemplary embodiment, the invention is implemented in software, which includes but is not limited to firmware, resident software, microcode, etc.

Furthermore, the invention may take the form of a computer program product accessible from a computer-usable or computer-readable medium providing program code for use by or in connection with a computer or any instruction execution system or device. For the purposes of this description, a computer-usable or computer readable medium may be any apparatus that can contain or store the program for use by or in connection with the instruction execution system, apparatus, or device.

The foregoing method may be realized by a program product comprising a Machine-readable medium having a machine-executable program of instructions, which when executed by a machine, such as a computer, performs the steps of the method. This program product may be stored on any of a variety of known machine-readable medium, including but not limited to compact discs, floppy discs, USB memory devices, and the like.

The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk an optical disk. Current examples of optical disks include compact disk-read only memory (CD-ROM), compact disk-read/write (CD-R/W) and DVD.

The preceding description and accompanying drawing are intended to be illustrative and not limiting of the invention. The scope of the invention is intended to encompass equivalent variations and configurations to the full extent of the following claims.

What is claimed is:

1. A method for removing artifacts from an EM field generator from a rotational 3D scan, comprising the steps of:
    preoperatively, characterizing the artifacts from the EM field generator over a range of rotational positions of an x-ray source and detector;
    intraoperatively, determining the position of the EM field generator relative to the x-ray source and detector; and
    removing the preoperatively characterized artifacts for the determined relative position of the EM field generator from a current x-ray image.

2. The method of claim 1, wherein characterizing the artifacts comprises determining the attenuation coefficients for each voxel of each artifact at each rotational position and wherein removing the preoperatively characterized artifacts comprises subtracting the attenuation coefficients from a current x-ray image.

3. The method of claim 2, further comprising the step of presenting the current x-ray image on a display with the artifacts removed.

4. The method of claim 3, wherein characterizing the artifacts further comprises determining the shape of each artifact.

5. The method of claim 4, wherein the shape of each artifact is determined by defining the artifacts using an edge detection process.

6. A system for removing artifacts from an EM field generator from a rotational 3D scan, comprising:
    a processor;
    a memory operably connected to the processor; and
    a program of instruction encoded on the memory and executed by the processor to:
    preoperatively, characterize the artifacts from the EM field generator over a range of rotational positions of an x-ray source and detector;
    intraoperatively, determine the position of the EM field generator relative to the x-ray source and detector; and
    remove the preoperatively characterized artifacts for the determined relative position of the EM field generator from a current x-ray image.

7. The system of claim 6, wherein characterizing the artifacts comprises determining the attenuation coefficients for each voxel of each artifact at each rotational position and wherein removing the preoperatively characterized artifacts comprises subtracting the attenuation coefficients from a current x-ray image.

8. The system of claim 7, further comprising a display operably connected to the processor, wherein the program of instruction when executed by the processor presents the current x-ray image on a display with the artifacts removed.

9. The system of claim 8, wherein the program of instruction executed by the processor further determines the shape of each artifact.

10. The system of claim 9, wherein the shape of each artifact is determined by defining the artifacts using an edge detection process.

11. A computer program product comprising a non-transient computer readable storage device having encoded thereon a computer executable program of instruction, comprising:
    program instructions for preoperatively, characterizing the artifacts from the EM field generator over a range of rotational positions of an x-ray source and detector;
    program instructions for intraoperatively, determining the position of the EM field generator relative to the x-ray source and detector; and program instructions for removing the preoperatively characterized artifacts for the determined relative position of the EM field generator from a current x-ray image.

12. The computer program product of claim 11, wherein the program instructions for characterizing the artifacts comprise program instructions for determining the attenuation coefficients for each voxel of each artifact at each rotational position and wherein the program instructions for removing the preoperatively characterized artifacts comprise program instructions for subtracting the attenuation coefficients from a current x-ray image.

13. The computer program product of claim 12, further comprising program instructions for presenting the current x-ray image on a display with the artifacts removed.

14. The computer program product of claim 13, wherein the program instructions for characterizing the artifacts further comprise program instructions for determining the shape of each artifact.

15. The computer program product of claim 14, wherein the program instructions for determining the shape of each artifact determine the shape of each artifact by defining the artifacts using an edge detection process.

\* \* \* \* \*